United States Patent [19]

Arbogast et al.

[11] Patent Number: 5,405,410

[45] Date of Patent: Apr. 11, 1995

[54] ADJUSTABLE LOWER LIMB PROSTHESIS HAVING CONICAL SUPPORT

[75] Inventors: Robert E. Arbogast, Mount Sterling; Eric K. Bartkus, Grove City; James M. Colvin, Hilliard; Joseph Arbogast, Mount Sterling, all of Ohio

[73] Assignee: Ohio Willow Wood Company, Mount Sterling, Ohio

[21] Appl. No.: 91,087

[22] Filed: Jul. 14, 1993

Related U.S. Application Data

[63] Continuation-in-part of Ser. No. 928,415, Aug. 12, 1992, abandoned.

[51] Int. Cl.⁶ .............................. A61F 2/62; A61F 2/76
[52] U.S. Cl. ............................ 623/47; 623/38; 623/53; 403/90; 403/281; 403/371
[58] Field of Search ............... 623/49, 48, 52, 53, 623/55, 47, 38, 50, 35; 403/90, 84, 222, 221, 227, 281, 362, 371

[56] References Cited

U.S. PATENT DOCUMENTS

| | | | |
|---|---|---|---|
| 608,812 | 8/1898 | Weller | 623/49 |
| 3,196,463 | 7/1965 | Farneth | 623/49 |
| 3,400,408 | 9/1968 | Garcia | 623/49 X |
| 3,659,294 | 5/1972 | Glabiszewski . | |
| 3,671,978 | 6/1972 | May . | |
| 3,982,278 | 9/1976 | May | 623/47 X |
| 5,047,063 | 9/1991 | Chen | 623/38 |
| 5,116,384 | 5/1992 | Wilson et al. | 623/49 |
| 5,139,524 | 8/1992 | Aulie et al. | 623/38 |

FOREIGN PATENT DOCUMENTS

| | | | |
|---|---|---|---|
| 0325333 | 9/1920 | Germany | 623/53 |
| 0550953 | 5/1932 | Germany | 623/53 |
| 0838480 | 5/1952 | Germany | 623/53 |
| 2605644 | 9/1976 | Germany . | |
| 3535812 | 3/1986 | Germany | 623/55 |
| 0427739 | 7/1948 | Italy | 623/53 |
| 2216423 | 10/1989 | United Kingdom | 623/53 |

OTHER PUBLICATIONS

Michael J. Quigley, Prosthetic Methods and Materials, Atlas of Limb Prosthetics, Surgical and Prosthetic Principles, American Academy of Orthopaedic Surgeons, The C.V. Mosby Company, 1981, Chapter 5, pp. 47–62.

*Primary Examiner*—David H. Willse
*Attorney, Agent, or Firm*—Oblon, Spivak, McClelland, Maier, & Neustadt

[57] ABSTRACT

An adjustable lower limb prosthesis has a pylon connected to both a prosthetic foot and to the stump adapter by way of a foot/pylon joint and a pylon/stump joint, respectively. Each of the joints is similar and includes a tapered socket holding a truncated conical wedge sleeve. The wedge sleeve has a bore which may be angled with respect to the cone axis, and into which the pylon is fitted. A cap locks the wedge sleeve in the bore and locks the pylon in the wedge sleeve. For adjusting the prosthesis, a set of wedge sleeves are available to the prosthetist, each having a bore with a different offset with respect to the conical axis of the sleeve. The prosthetist selects the appropriate sleeve based upon a prior determination using a temporary pylon and an alignment adapter. The correct foot wedge sleeve and circumferential alignment of the wedge sleeve are set with the aid of discs having offset holes.

11 Claims, 7 Drawing Sheets

ADJUSTABLE LOWER LIMB PROSTHESIS HAVING CONICAL SUPPORT

This application is a Continuation-In-Part of application Ser. No. 07/928,415, filed Aug. 12, 1992, now abandoned.

BACKGROUND OF THE INVENTION

1. Field of the Invention

The present invention is directed to a lower limb prosthesis. More particularly, the present invention is directed to the adjustment of a lower limb prosthesis to suit the ambulatory characteristics of the amputee to which it is to be fitted.

2. Background of the Related Art

Lower limb prosthetic devices are presently comprised of two basic classifications. One classification, termed exoskeletal prosthetic devices, relates to devices where the vast majority of the vertical load of the amputee is supported by the shell of the prosthetic appliance. This shell has basically the same exterior shape as did the lost limb, and is usually manufactured from a combination of wood and rigid thermoset plastics reinforced with some type of long fiber, to which a separate prosthetic foot may be attached. This construction renders the prosthesis hard to the touch, but it may be coated with a thin layer of flexible material for cosmetic reasons.

The second type of lower limb prosthetic appliance is termed endoskeletal. This classification relates to a device which carries the vast majority of the vertical load through an inner supporting member or pylon. This inner member has a shape totally unrelated to that of the missing limb and is consequently covered with a light weight flexible foam which is then given the proper shape. This structure may or may not include an attached prosthetic foot. If a prosthetic foot is not included in the basic design, a separate prosthetic foot is attached.

A common type of below knee prosthetic device of the endoskeletal type is comprised of separate foot and shin members, which may be fabricated from components of different manufacturers due to modular design features that exist in much of the componentry available today. This appliance consists of a rigid tube (pylon) made of metal or thermosetting composite material attached to a custom fabricated cup or socket which contains the residual limb. At the other or lower end of this rigid structural tube is the prosthetic foot.

Walking is a complex movement which involves not only the pivoting of the lower limb around the knee joint, but also the rotation of the lower limb about its length. Moreover, lower limbs are not perfectly straight but are slightly bent and twisted by amounts unique to a given individual. It is therefore common practice to provide lower limb prostheses with angular adjustments tailored to the comfort and gait of the amputee. For this purpose, before receiving a permanent prosthesis the amputee is given a "temporary leg." This is a somewhat cumbersome device containing many adjustable features to help determine the proper alignment for the amputee. After a sufficient amount of time walking on the temporary leg, the prosthetist is able to determine the proper relationship between the prosthetic foot and the socket mounted to the residual limb. This temporary leg is then placed in an apparatus called a bench mounted alignment fixture, a device common to the industry. The socket, which can be reused, is positioned and held firmly by this device and the position of the foot relative to this socket is then noted and recorded. The temporary leg, with the exception of the socket, is removed from the bench mounted alignment fixture, making the socket ready for the installation of a permanent prosthesis.

A conventional permanent prosthesis uses regularly adjustable adapters at the end of a rigid tube. An example may be found in British Patent Specification 978,586 which uses a pair of lockable ball joints at the ends of a tube and connecting the tube to both the prosthetic foot and the socket. U.S. Pat. No. 3,659,294 (Glabiszewski) uses adjustable joints which are adjusted by screws. Although such adapters give the prosthesis the advantage of adjustability, they have the pronounced disadvantages of added weight and the possibility of failure due to the mechanical fasteners becoming loosened during normal usage.

More recently, U.S. Pat. No. 5,133,777 having the same assignee as the present application and being incorporated herein by reference, disclosed an adjustable lower limb prosthesis which avoids the disadvantages of the prior art. There, a pylon rod is formed of unidirectional long fibers embedded in a thermoplastic matrix and the foot is connected directly to the pylon. Adjustment is provided by selectively heating portions of the pylon to a temperature above the softening temperature of the thermoplastic matrix, bending the pylon to the correct alignment and permitting the pylon to cool. Since the adjustable (e.g., ball) joints of the prior art need not be used, the disadvantages of high weight and possible failure due to mechanical fasteners becoming loosened are avoided.

The prosthesis disclosed in U.S. Pat. NO. 5,133,777 is particularly advantageous for active amputees such as joggers and other sports enthusiasts because the pylon having unidirectional long fibers in a thermoplastic matrix acts as a torsional spring for limited and controlled rotation of the prosthetic foot relative to the socket during ambulation of the amputees and because the thermoplastic resin is able to damp vibrations from reaching the socket. On the other hand, less active amputees have less of a requirement for vibration damping and the torsional spring effect of a pylon made of unidirectional long fibers encased in a thermoplastic matrix. It is therefore desirable to provide an adjustable lower limb prosthesis which can use a less expensive pylon, yet which avoids the high weight and low reliability problems of the prior art. It is also beneficial to provide a lower limb prosthesis which is easy to align, transfer, and finish with a cosmetic cover to reduce labor costs associated with the assembly of the prosthesis.

SUMMARY OF THE INVENTION

It is an object of the invention to provide a low cost, light weight lower limb prosthesis having high reliability.

It is a further object of the invention to provide a method for adjusting a low cost, light weight prosthesis having high reliability.

According to a feature of the invention, a lower limb prosthesis comprises a prosthetic foot, a rodlike pylon, a foot/pylon joint and a pylon/stump joint. The foot/pylon joint comprises a tapered socket extending into the foot, a truncated conical sleeve snugly fitted into the socket of the foot, the sleeve having a bore extending thereinto, the pylon being snugly fitted in the bore, and means for locking the sleeve in the socket and locking the pylon in the bore. The pylon/stump joint comprises an adapter to be mounted to the stump of a residual lower limb, the stump adapter having another tapered socket, another truncated conical sleeve, the sleeve having another bore extending thereinto, the pylon being snugly fitted in the another bore, and means for locking the another sleeve in the another socket and locking the pylon in the another bore.

According to another feature of the invention, a prosthesis comprises a prosthetic part, a joint for connecting the prosthetic part to a pylon, the joint comprising a shell forming a socket in the prosthetic part, a pylon fittable in the socket and means mountable in the socket for securing the pylon in the socket at a fixed angular orientation relative to the socket so that it does not pivot. The socket has an open top, a substantially conical tapered wall and a hemispherical bottom.

According to one embodiment, the means for securing the pylon in the socket is a conical sleeve snugly fittable in the socket. According to another embodiment, the means for securing the pylon in the socket is an adjustment adapter having at least three screws abutting the pylon.

According to another feature of the invention, a method of adjustment of a prosthetic lower limb assembly for an amputee, the assembly including a prosthetic foot and a rodlike pylon, comprises the steps of mounting a temporary pylon to at least one of the prosthetic foot and an adapter for the stump of a lower limb via a temporary joint portion having an adjustable adapter member to form a temporary prosthesis, permitting the amputee to walk using the temporary prosthesis, adjusting the alignment of the pylon with respect to an axis of the adapter member, determining adjustment data from the adjusted adapter member, selecting a permanent joint portion having a nonadjustable characteristic, a value of which is selected as a function of the determined adjustment data, and connecting a permanent pylon to the at least one of the prosthetic foot and the stump via the permanent joint portion.

According to yet a further feature of the invention, there are provided a set of conical sleeves comprising a plurality of sleeves, each of which comprises a cone part having a truncated conical outer periphery, a bore extending through the cone part, the bores of at least some of the sleeves being angled with respect to the axis of the conical periphery such that a bore axis and a cone axis substantially coincide at a small diameter end of the cone part and such that the bore axis is offset from the cone axis at a large diameter end of the cone part, wherein at least some of the sleeves have different offsets. A slot connects the bore with the outer periphery at a circumferential position where the bore is substantially closest to the outer periphery.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

In the following, nonlimiting, example, the same reference numerals will be used to reference the same or corresponding parts throughout the several views.

Figure 1:
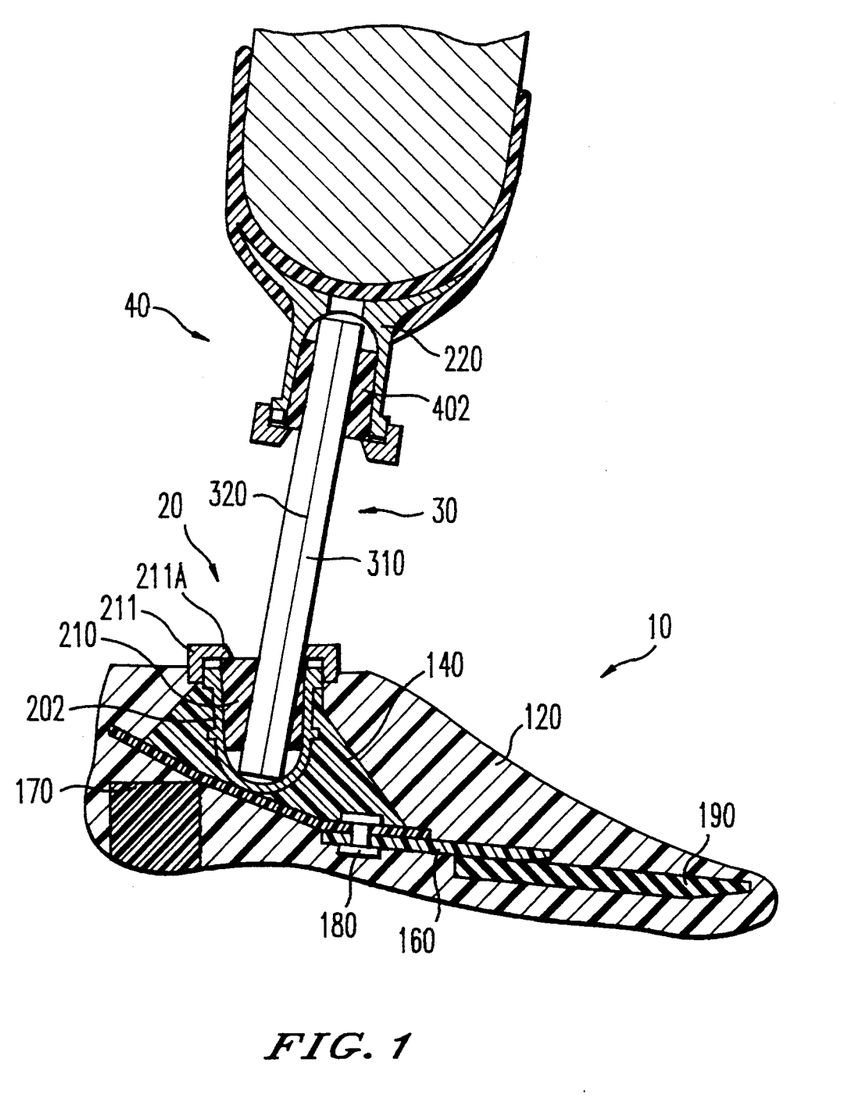
FIG. 1 is a sectional elevation view showing the prosthetic device according to the present invention.

FIG. 1 shows in section a lower limb prosthesis according to the present invention. The prosthesis has four major components: a prosthetic foot 10, a foot/pylon joint 20, a pylon 30 and a pylon/stump joint 40. These major components will now be described in sequence.

The specific construction of the prosthetic foot 10 is not critical to the invention. For example, the foot may be similar in heel and toe design to a SACH foot of the type manufactured by Kingsley Mfg. Co. of Costa Mesa, Calif. In a preferred embodiment, the foot 10 is formed of a flexible foam urethane number 120 which can have a cosmetic "skin" covering and which is molded around a keel 140 formed of thermoset sheet molding compound (SMC).

One or more composite deflection plates 160 are riveted to the keel. The plate 160 is also formed of SMC material. It has two layers: a lower layer formed of unidirectional continuous E glass fibers which supports the tensile bending loads during walking, and an upper layer of random chopped E glass fibers which performs well in compressive bending fatigue and provides good reinforcement around the rivet holes. Both layers use vinylester resin (with 5-10 min. curing time at mold temperature of 280° F.) as a binder. The plate 160 is riveted to the keel 140 at rivet 180.

The reinforced rubber belting 190 extends from the plate 160 to which it is secured by an adhesive, toward the toe of the foot to provide additional strength and resilience to the toe area. A heel wedge 170 is formed of a urethane material having an appropriate stiffness. The heel wedge 170 may have small holes drilled therein to reduce stiffness. Optionally, the heel wedge 170 can be made interchangeable to provide varying degrees of stiffness. Cylindrical heel wedges could be inserted into a circular hole in the bottom exterior foam surface of the foot and adhesively attached.

The foot/pylon joint 20 includes a shell 202, usually formed of aluminum. The shell 202 is molded within the keel 140 and so is unitary with the foot 10. The shell defines an internal truncated conical socket 204 (FIG. 3) having a hemispherical bottom 206 with a center C. An annular flange 207 at the top of the shell 202 has outer screw threads (not shown) and an annular top surface into which extends an alignment hole 208. The shell 202 is molded into the keel such that the alignment hole 208 is positioned to indicate the forward direction, i.e., it is generally on a plane which extends through the centerline 201 of the shell and which is parallel to the median longitudinal plane of the foot.

Figure 3:
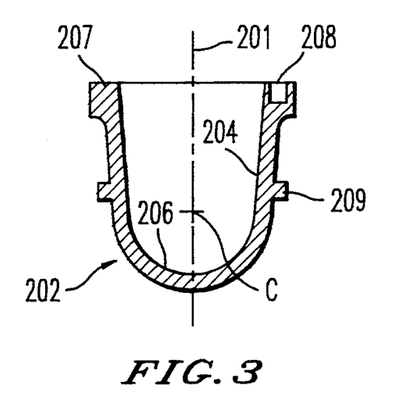
FIG. 3 is a sectional view of the foot mounted socket shell of an embodiment of the invention.

A retainer ring 209 is integrally formed with the external surface of the shell 202 to help retain the shell within the keel. It includes one or more "flats" which prevent rotation of the shell within the keel.

Figure 7A:
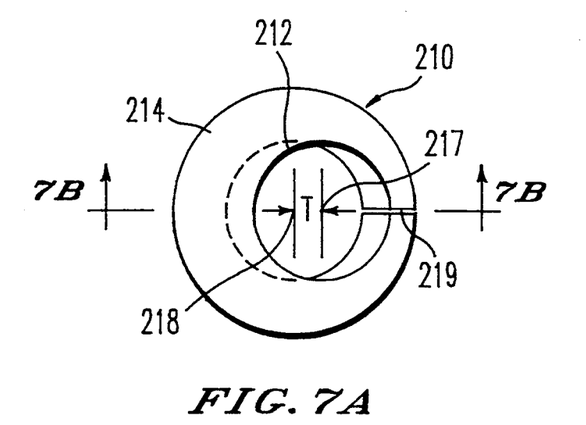
FIG. 7A is a top plan view of a wedge sleeve of the lower limb prosthesis of an embodiment of the invention.
Figure 7B:
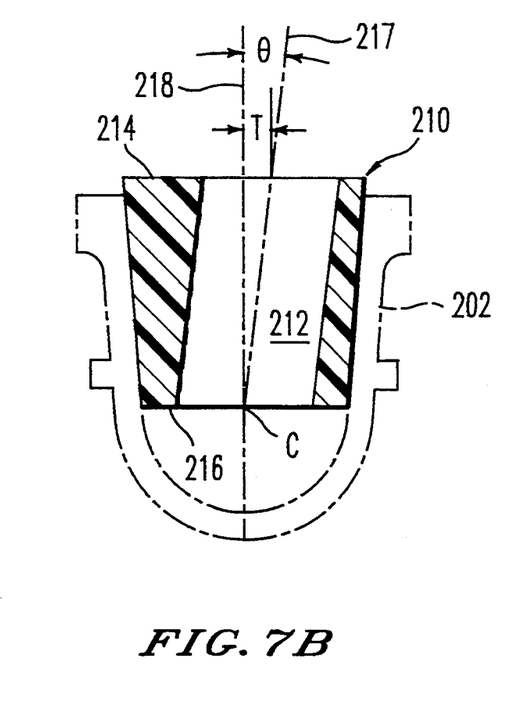
FIG. 7B is a sectional elevation view of the wedge sleeve of FIG. 7A, taken along line 7B—7B, inserted into the foot mounted socket shell of FIG. 3.
Figure 8A:
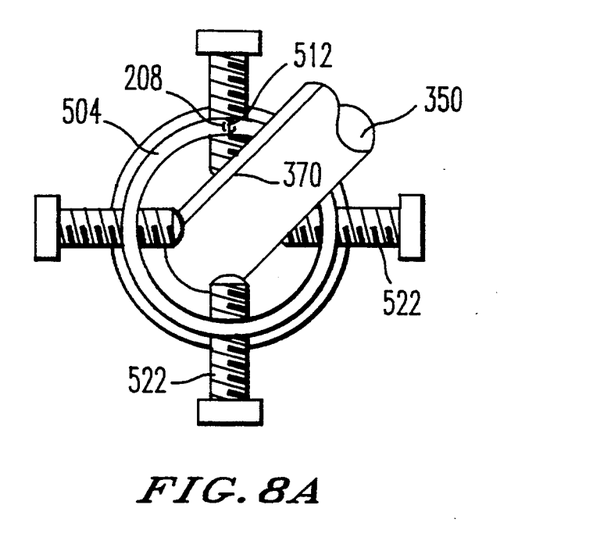
FIG. 8A is a schematic plan view of an adjustment rod positioned in the alignment sleeve of FIG. 5 during an adjustment procedure.
Figure 8B:
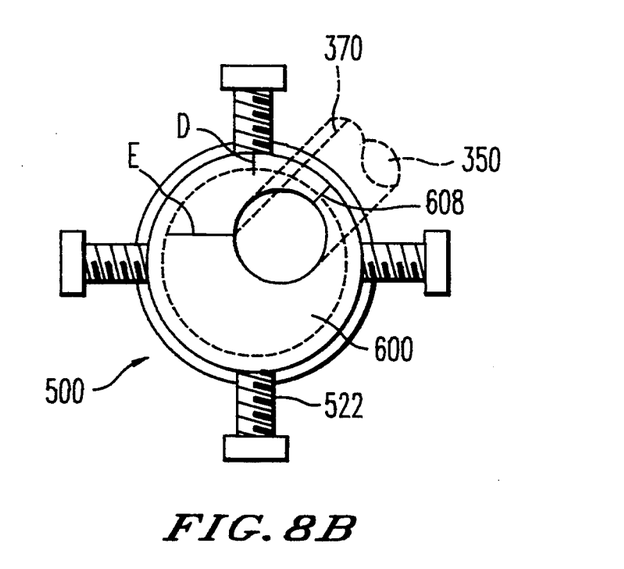
FIG. 8B shows the alignment sleeve of FIG. 8A with an appropriate measurement disc according to FIG. 6 placed thereupon, the adjustment rod being shown in dash lines.
Figure 8C:
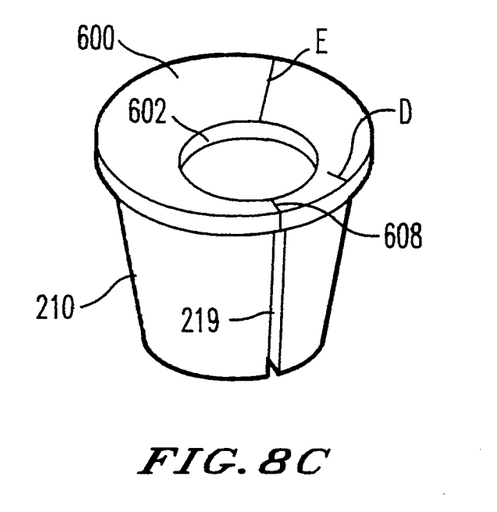
FIG. 8C shows a perspective view of the measurement disc of FIG. 8B positioned on a selected wedge sleeve.
Figure 8D:
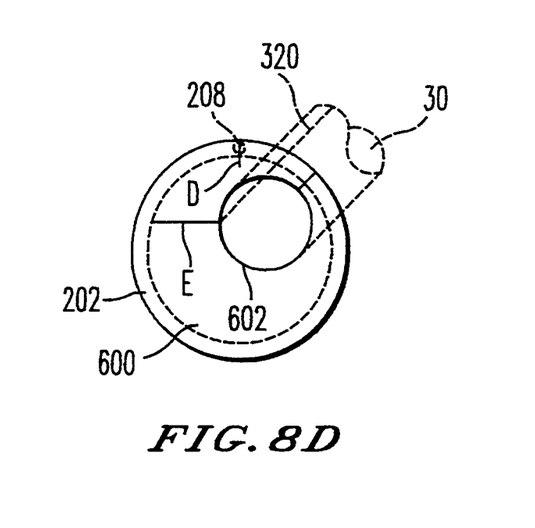
FIG. 8D shows a plan view of the wedge sleeve and measurement disc of FIG. 8C mounted within the foot socket shell, the pylon being shown in dash lines.

The foot/pylon joint also includes a wedge sleeve (permanent joint portion) 210. As best seen in FIGS. 7A, 7B and 8C, the wedge sleeve 210 is in the form of a truncated conical section tapered at the same angle as the socket 204 of the shell 202 so that the sleeve 210 can snugly fit into the shell. The sleeve 210 is also formed of SMC.

The sleeve 210 has a cylindrical bore 212 extending entirely therethrough from the large diameter top end surface 214 to the small diameter bottom end surface 216 thereof. The bore in FIG. 7B has an axis 217 which is tilted in by an angle $\theta$ with respect to the axis 218 of the conical outer surface of the sleeve 210. The bore 212 is formed in the sleeve 210 such that its axis 217 intersects the cone axis 218 of the sleeve at a point substantially coincident with the bottom surface 216 which is substantially at the center C of the hemispherical bottom surface 206 of the socket 204 when the sleeve 210 is fully fitted within the socket 204. The bore therefore has an offset T with respect to the axis 218 at the location of the top surface 214.

A slot 219 connects the bore 212 with the outer peripheral surface of the sleeve 210 at the circumferential position where the thickness of the sleeve material between the bore and the outer surface is the smallest.

A locking nut 211 (FIG. 1) is threaded onto the flange 207 of the shell and has an inner flange 211A which clamps onto the top surface 214 of the wedge 210 so as to hold the wedge within the socket 204, and further push the wedge 210 into the socket 204 as the locking nut is tightened.

The pylon 30 is a rod having a substantially circular section and is pultruded from E glass or carbon fibers with a thermosetting or thermoplastic resin matrix. Pultrusion provides the benefits of low cost, good dimensional stability and adequate mechanical properties. The good dimensional stability is critical due to the secure fit between the rod and the bore in the wedge sleeve 210. The pultruded rod is also easy to cut to a desired length. In an especially preferred embodiment, the pylon has a longitudinal alignment mark 320, whose purpose will be described below.

As best seen in FIG. 1, the pylon 30 snugly fits into the bore 212 of the wedge sleeve 210 and rests on the hemispherical bottom 206 of the shell 202. Although not shown, the edge of the end of the pylon 30 may be bevelled to prevent damage to the end, or to prevent the edge from damaging the surface of the bottom 206.

Tightening of the locking nut 211 forces the wedge sleeve 210 farther into the socket 204, which, because of the taper of the socket, causes slot 219 to close and the wedge sleeve 210 to securely clamp or lock the pylon 30.

Figure 4:
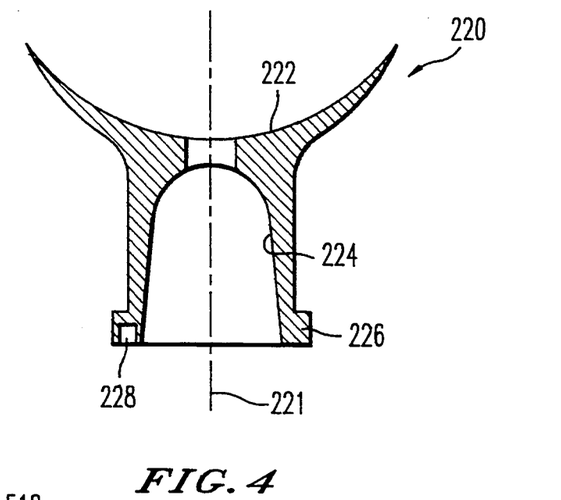
FIG. 4 is a sectional view of the stump adapter of an embodiment of the invention.

The pylon/stump joint 40 is similar to the foot/pylon joint 20 in that it includes a member forming a socket for accepting a wedge sleeve 402 identical to the wedge sleeve 210 (except, possibly, for the offset value T). A stump adapter 220 (FIG. 4) has a conventional stump engaging portion 222 but terminates in a tapered cylindrical socket 224 identical to the socket 204 of the shell 202 in the foot/pylon joint. The stump adapter 220 also includes a flange 226 like the flange 207, the annular end surface of the flange 206 having a hole 228 identical to, and for the same purpose as, the hole 208 of the shell 202. The hole 228 is also to be aligned in a forward direction, for the reasons to be described below.

The adjustment of the prosthesis described above will normally involve three types of adjustment: The angle and circumferential orientation of the offset of the longitudinal axis of the pylon with respect to the axis 201 of the shell socket 204; the corresponding angle and circumferential offset of the longitudinal axis of the pylon with respect to the axis 221 of the adapter socket 224; and the "toe-out" i.e., the angle by which the longitudinal median plane of the prosthetic foot is offset from the fore and aft direction when the amputee is standing at rest. The "toe-out" of the prosthetic foot should be the same as that for the other foot.

The following will describe the adjustment sequence for the foot/pylon joint adjustment, followed by that for the pylon/stump joint, although the order of adjustment could be reversed.

Initially, a temporary or adjustment rod 350 is placed in the socket 204 of the shell 202. The adjustment rod is selected from a set of adjustment rods of different lengths. The length of the adjustment rod is selected to be appropriate for the amputee. The adjustment rod 350 could be identical to the pylon 30, but could instead be made of metal or a combination of pylon 30 and metal. Optionally, a nylon ball 360 having a diameter corresponding to that of the hemispherical bottom 206 could be placed on the end of the adjustment rod which fits into the socket 204, to permit easy rotation during adjustment. Like the pylon, the adjustment rod has a longitudinal alignment mark 370 along its length (FIG. 8A). Also optionally, the adjustment rod could have a variable length.

Figure 5:
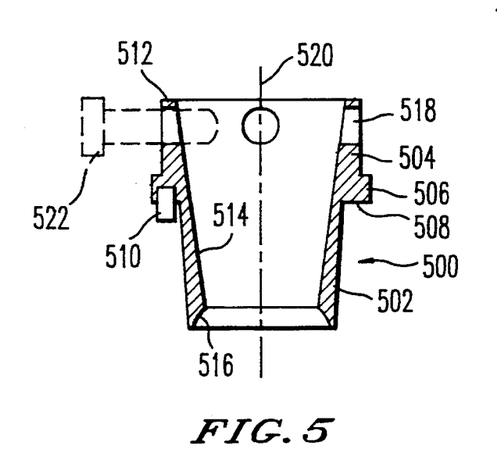
FIG. 5 is a sectional view of an alignment device used in an embodiment of the invention.

An alignment adapter 500 (FIGS. 2 and 5) is then placed over the adjustment rod and mated with the shell 202 to form a temporary joint portion. As seen in FIG. 5, the alignment adapter may have a generally truncated conical lower portion 502 which mates snugly with the tapered surface of the socket 204. A generally cylindrical upper portion 504 may join the lower portion at an annular ring 506 defining a shoulder 508. When the alignment adapter 500 is placed on the shell 202, the shoulder 508 rests on the annular top surface of the flange 207. A dowel pin 510 fits into the hole 208 of the shell in order to circumferentially align the alignment adapter 500 with the shell 202. A permanent mark or groove 512 on the annular top surface of the alignment adapter 500 is circumferentially aligned with the dowel pin 510, and so is circumferentially aligned with the hole 208.

Figure 2:
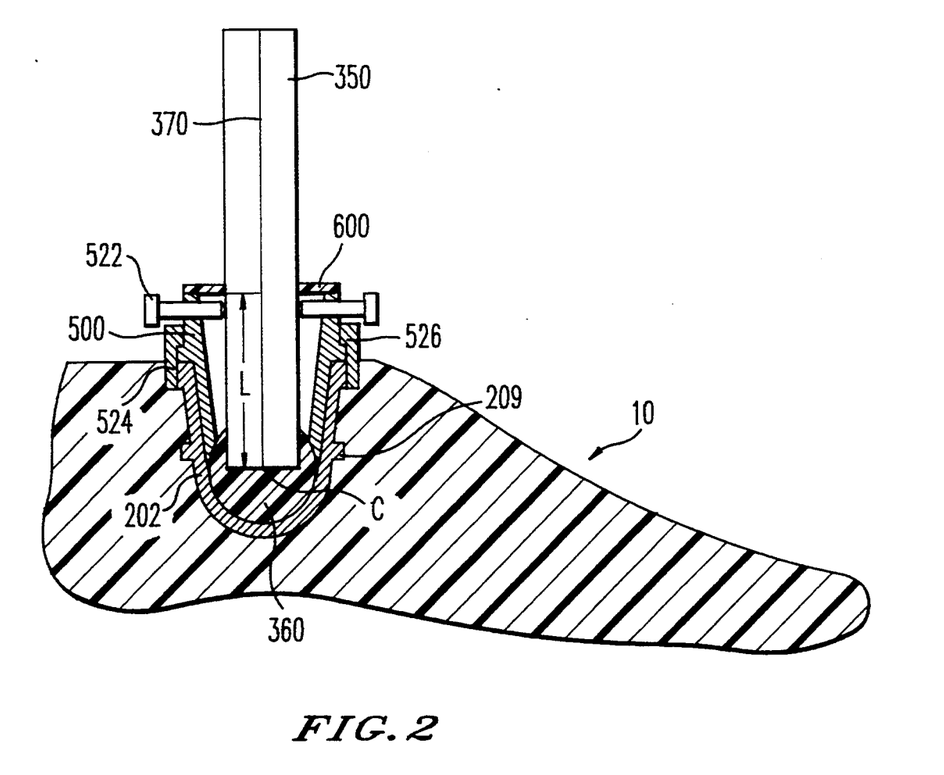
FIG. 2 is a sectional elevation view showing a lower portion of the prosthetic device during adjustment.

A tapered bore 514 may extend through the alignment adapter from the top to the bottom thereof. The lower edge of the bore 514 can optionally terminate a spherical section bevel 516 which forms a bearing surface for the optional nylon ball 360 (FIG. 2).

An alignment cap 524 (FIG. 2) is then threaded onto the flange 207 and has a radially extending flange part 526 which clamps onto the ring 506 of the alignment adapter to securely hold the same onto the shell 202 during adjustment, with the axis 520 of the adapter 500 colinear with the axis 201 of the shell 202.

Four threaded holes 518 (only three are shown in FIG. 5) are formed through the wall of the alignment adapter near the top thereof. The four holes lie in pairs on mutually orthogonal axes which pass perpendicularly through the axis 520 of the alignment adapter, so that the holes are circumferentially spaced by 90 degrees. Adjustment screws 522 are threaded into each of the holes 518. The adjustment screws can have brass tips to prevent marring of the adjustment rod 350. The adjustment rod can also have protective sleeves where the screw tips bear thereon.

An identical arrangement is then provided for the socket 224 of the stump adapter 220, thereby producing a temporary prosthesis.

Subsequently, the amputee is permitted to walk with the temporary prosthesis having the adjustment rod and the alignment adapters, and adjustment is made to both alignment adapters for the particular gait and "toe-out" of the amputee. This is done by manipulating the adjustment screws 522 of both alignment adapters to set a desired angle and circumferential orientation for the offset of the longitudinal axis of the adjustment rod 350 with respect to the longitudinal axes of the shell 202 and stump adapter 220 (FIG. 8A).

Although not shown, the adjustment rod 350 has four flats at one end (e.g., the end for the foot adapter) against which the screws of the respective alignment adapter 500 bear. This prevents rotation of adjustment rod relative to that alignment adapter.

The alignment cap 524 for the socket adapter is then loosened to allow ball 360 to rotate, two adjacent setscrews are slightly loosened, the pylon and foot are rotated for the correct "toe-out" and the setscrews and alignment cap are subsequently retightened.

Once adjustment has been completed, the correct adjustment data must be determined, recorded and transferred to a permanent prosthesis. A novel technique for so doing is set forth below.

Figure 6:
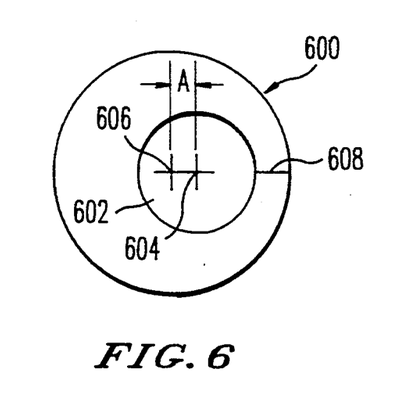
FIG. 6 is a plan view of a measurement disc used in the adjustment of the lower limb prosthesis of an embodiment of the invention.

The prosthetist first chooses a correct transfer disc 600 (FIG. 6) from a set of such transfer discs which are available to the prosthetist. Each disc is formed of transparent nylon or some other elastic transparent material, and each has an outer diameter identical to that of the top end surface 504 of the alignment adapter 500. Each transfer disc has a circular hole 602 having a diameter identical to that of the adjustment rod 350.

A plurality of different alignment discs are provided in a set. Each of the discs is identical except for the position of the center 604 of the hole 602 with respect to the center 606 of the disc. The exemplary disc of FIG. 6 has a hole center 604 offset by the distance A from the center 606. Each of the discs is marked with a designation corresponding to its offset, so that one can identify the offset of the disc by referring to that designation. For example, there may be nine different discs marked "zero" to "eight" which could correspond to zero to eight degrees of angular offset of the alignment rod.

Thus, for a number eight disc the offset A is equal to L sin 8° (see FIG. 2).

Once the prosthetist has chosen a disc having an offset which matches that of the adjustment rod 350, the disc is placed over the rod. This is done for both the foot/pylon joint and the pylon/stump joint. For this purpose, the disc has a slit 608 which extends between the hole 602 and the outer periphery of the disc. The slit 608 is at the circumferential portion of the disc where the hole is closest to the periphery, i.e., on a line connecting centers 606 and 604. Once mounted on the adjustment rod 350, the disc 600 is rotated thereon until its outer periphery is perfectly centered on the cylindrical upper portion of the alignment adapter 500 (FIG. 8B). At this time, marks D and E are made on the top surface of the disc 600. The mark D indicates the position of the alignment mark 512 on the top surface of the alignment adapter 500, and so marks the location of the alignment hole 208 of the shell 200. The mark E indicates the position of the longitudinal alignment mark 370 on the adjustment rod 350.

Once the marks D and E have been made, the alignment adapter 500 and the adjustment rod 350 are removed from the foot 10, as is the disc 600. At this time, the prosthetist selects a wedge sleeve 210 corresponding to the designated disc 600. Just as there are a plural number of discs 600 having different offsets A, each disc having a designation, there are a plural number of wedge sleeves 210, which have designations of the offset T. A wedge sleeve having an offset T which positions the pylon 30 at offset A of a given disc will have the same designation as that disc, and so it is a simple matter to select a correct wedge sleeve by reference to the designation on the chosen disc. Thus, for example, a number 8 wedge sleeve and a number 8 disc will both have an identical angular offset, with the linear offset determined by the distance from the center of rotation.

The disc 600 having the marks D and E thereon is then placed on the top end surface 214 of the corresponding wedge sleeve 210 and rotated so that the slit 608 aligns with the slot 219 (FIG. 8C). This assembly is then loosely placed in the socket 204 of the shell 202. The wedge sleeve 210 is then rotated, with the slit 608 and the slot 219 being kept in alignment, until the mark D is aligned with the hole 208. The offset of the wedge disc is thus correctly circumferentially oriented on the shell 202.

A pylon 30 having the same length as the adjustment rod 350 is then selected and inserted into the bore 212 of the wedge sleeve until its end bears on the hemispherical bottom 206 of the shell 202. The pylon 30 is then rotated until the alignment mark E aligns with the longitudinal alignment mark 320 on the pylon. The disc 600 is then removed and the locking nut 211, which had previously been placed on the pylon 30, is screwed onto the screw threads of the flange 207 to lock the wedge sleeve into the shell, and tighten the wedge sleeve onto the pylon.

A similar procedure is then performed for the pylon/stump joint. At this time, the alignment of marks E and 320 sets the correct "toe-out" for the prosthesis.

The resulting prosthesis has high reliability and simple construction. The wedge sleeves have a nonadjustable offset angle and are securely locked down by the locking nuts. Loosening of the joint settings is therefore difficult or impossible. Moreover, the pultruded thermoset plastic pylons are light weight and inexpensive as compared to the thermoplastic pylons of the copending application 07/512,260. This results in a prosthesis which is ideal for less active amputees who have no need for the higher vibration damping and torsional spring characteristics of the prosthesis of the related application.

As described in the above embodiments, once the correct adjustment data is determined using the alignment adapter 500, the alignment adapter 500 is removed and replaced by an appropriate wedge sleeve 210. This is necessary primarily to prevent damage to the pylon during extended wear by the amputee.

A pylon formed of glass or carbon fibers in a resin matrix, such as the pylon 30, is preferable to a metal pylon, due to the energy absorbing characteristics of the fiber/resin pylon which are favorable for smooth ambulation. However, a fiber/resin pylon is highly anisotropic and has little resistance to damage from forces acting in a direction transverse to the length of the pylon. Therefore, if one were to permit the amputee to use a prosthesis having a fiber/resin pylon 30 supported and fixed merely by the adjustment screws 522 of the alignment adapter 500 on a long term basis, the pylon could be damaged by the localized transverse pressures of the screws bearing on the pylon. The wedge sleeves 210, on the other hand, grip the pylon 30 over a relatively wide area, and the resulting reduced local pressure reduces the likelihood of pylon damage.

Figure 2A:
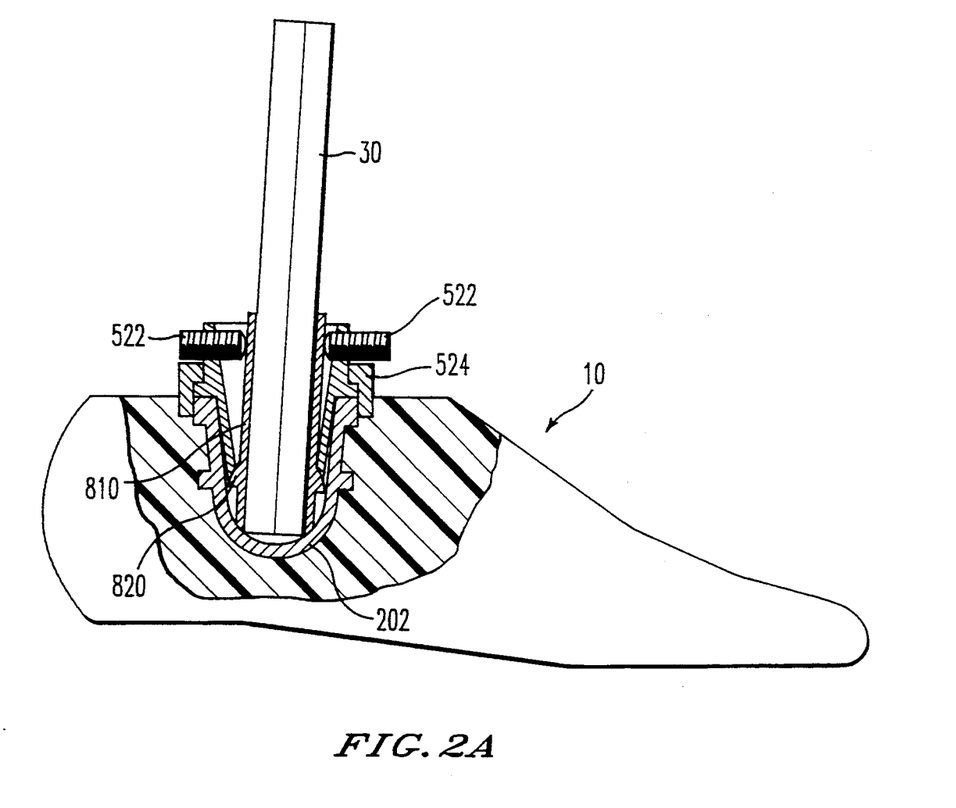
FIG. 2A corresponds to FIG. 2 but shows another embodiment.

In view of the above, a second embodiment retains the alignment adapter 500 in the permanent prosthesis but protects the pylon against high local pressures produced by the adjustment screws 522. In the embodiment of FIG. 2A, the pylon 30 is provided with a stainless steel sleeve 810 to which it is permanently bonded or adhered. The stainless steel sleeve 810 has a partially spherical lower portion, including a partially spherical boss 820, thereby providing a substitute for the ball 360 of FIG. 2. More significantly, the adjustment screws 522 abut the sleeve 810 which distributes the pressures of the screws over a wide area to prevent deterioration of the pylon during long term ambulation by the amputee.

Therefore, according to this alternative embodiment no temporary adjustment rod 350 is used. Instead, the permanent pylon 30 having the sleeve 810 thereon is placed in the alignment adapter 500 and adjustment is made in the same way as in the first embodiment.

Although not shown, the sleeve 810 may also have four flats against which the screws of the alignment adapter 500 bear to prevent rotation of the pylon relative to the alignment adapter.

Once adjustment has been completed, the prosthesis is complete and ready for long term use by the amputee. No transfer of adjustment data to a permanent prosthesis is thus necessary.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A prosthesis comprising:
   a prosthetic part;
   a pylon;
   a joint for connecting said prosthetic part to said pylon, said joint comprising a shell forming a socket in said prosthetic part, said socket having an open top into which said pylon is fittable, a substantially conically tapered wall and a hemispherical bottom;
   a conical sleeve snugly fittable in said socket, said sleeve having a substantially conical outer peripheral surface, a bore extending generally axially to the outer peripheral surface for accepting the pylon, and a substantially radially extending slot connecting the bore to the outer peripheral surface of said sleeve, wherein the bore of said sleeve is offset with respect to the axis of the outer peripheral surface; and
   means for locking the sleeve in the socket such that the sleeve is pressed into the socket and the width of the slot is reduced, whereby the pylon in the bore is securely gripped thereby and does not pivot at said joint.

2. The prosthesis of claim 1 wherein said locking means comprises a cap threaded on said tapered socket.

3. The prosthesis of claim 1 including the pylon fitted in said bore.

4. The prosthesis of claim 1 wherein said prosthetic part is a foot part.

5. The prosthesis of claim 1, wherein the slot of said conical sleeve is circumferentially positioned substantially where the bore is closest to said outer peripheral surface.

6. A prosthesis comprising:
   a prosthetic part;
   a pylon formed of reinforcing fibers in a resin matrix;
   a joint for connecting said prosthetic part to said pylon, said joint comprising a shell forming a socket in said prosthetic part, said socket having an open top into which said pylon is fittable, a substantially conically tapered wall and a hemispherical bottom;
   an adaptor fixed in said socket;
   a substantially cylindrical metal sleeve on said pylon; and
   at least three screws threaded into said adaptor and abutting the sleeve at a surface portion thereof which is substantially cylindrical, such that said pylon is maintained at a fixed angular position relative to said socket and does not pivot at said joint.

7. The prosthesis of claim 6 including a partially spherical portion on said pylon in said socket.

8. The prosthesis of claim 7 wherein said partially spherical portion is formed on said sleeve.

9. A prosthesis comprising:
   a prosthetic part;
   a pylon;
   a joint for connecting said prosthetic part to said pylon, said joint comprising a shell forming a socket in said prosthetic part, said socket having an open top into which said pylon is fittable;
   a sleeve snugly fittable in said socket, said sleeve having a wall with an outer peripheral surface, a bore extending generally axially to the outer peripheral surface for accepting the pylon, and a slot extending substantially radially through said wall and connecting the bore to the outer peripheral surface of said sleeve, wherein the bore of said sleeve is offset with respect to the axis of the outer peripheral surface; and
   means for locking the sleeve in the socket such that the sleeve is pressed into the socket and the width of the slot is reduced, whereby the pylon in the bore is securely gripped thereby and does not pivot at said joint.

10. The prosthesis of claim 9 wherein said socket and said sleeve have mating tapered portions.

11. A prosthesis comprising:
 a prosthetic part;
 a pylon formed of reinforcing fibers in a resin matrix;
 a joint for connecting said prosthetic part to said pylon, said joint comprising a shell forming a socket in said prosthetic part, said socket having an open top into which said pylon is fittable, an adaptor, a substantially conically tapered wall and a hemispherical bottom;
 a substantially cylindrical metal sleeve on said pylon; and
 at least three screws threaded into said adaptor and abutting the sleeve at a surface portion thereof which is substantially cylindrical, such that said pylon is maintained at a fixed angular position relative to said socket and does not pivot at said joint.

\* \* \* \* \*